United States Patent [19]
Rudzki

[11] Patent Number: 4,747,645
[45] Date of Patent: May 31, 1988

[54] ILLUMINATION SYSTEM FOR MATERIAL TESTING APPARATUS

[75] Inventor: Thore Rudzki, Hanau, Fed. Rep. of Germany

[73] Assignee: W. C. Heraeus GmbH, Hanau, Fed. Rep. of Germany

[21] Appl. No.: 828,830

[22] Filed: Feb. 12, 1986

[30] Foreign Application Priority Data

Feb. 13, 1985 [DE] Fed. Rep. of Germany ....... 3504793

[51] Int. Cl.$^4$ ............................ G21K 5/00; G02B 5/10
[52] U.S. Cl. ................................... 350/1.1; 250/492.1
[58] Field of Search ...................... 350/1.1; 250/492.1

[56] References Cited

U.S. PATENT DOCUMENTS 3,686,940  8/1972  Kockott .

OTHER PUBLICATIONS

"Xenotest 1200" Product Brochure, published by W. C. Heraeus GmbH.

Primary Examiner—Bruce Y. Arnold
Attorney, Agent, or Firm—Frishauf, Holtz, Goodman & Woodward

[57] ABSTRACT

To separate ultraviolet (UV) radiation emitted from a light source (9) from impinging on infrared (IR) filters, in which the respective filters filter the radiation from the light source to result in controlled spectral distribution simulating, at least approximately, sunlight, an outer UV filter (10) is located in a first section, adjacent a first mirror-filter combination (11), alternatingly located in polygonal form, for example square (FIG. 2) or triangular (FIG. 3) or in cylindrical form (FIGS. 5,6) surrounding the light source. The first mirror-filter combination includes a first UV mirror (12) having its mirror surface directed towards the light source and, externally thereof, a IR filter (13). A sandwich assembly of a second mirror-filter combination (14) is located interiorally of the sections, the sandwich assembly having an inner UV mirror (15), reflecting inwardly, an outer UV mirror (16) reflecting outwardly, and a IR filter (17) located intermediate the mirrors, the second mirror-filter combination being so positioned with respect to the UV filter (10) to place the UV filter entirely within the optical shadow of radiation emitted from the light source, so that the radiation is separated into UV and IR and visible light components, UV radiation being passed only through the UV filter and prevented from reaching any IR filter.

17 Claims, 6 Drawing Sheets

Fig: 4

ILLUMINATION SYSTEM FOR MATERIAL TESTING APPARATUS

The present invention relates to apparatus to test resistance against the influences of light and weathering on samples of goods, such as paint, fabrics, or other material, and more particularly to provide an apparatus which can accurately reproduce spectral conditions under controlled circumstances, for example simulating sunlight with controlled ultraviolet (UV) and infrared (IR) components, that is, sunlight which might occur under various atmospheric conditions and geographic locations, e.g., at sea level, high altitudes, or the like.

BACKGROUND

The Assignee of the present application is the manufacturer of a rapid illumination and weather testing apparatus trademarked "Xenotest 1,200" ®, and described, for example, in literature material D310 561/681. The apparatus permits checking of various and highly different materials with respect to resistance to fading due to light and weather, or other environmental effects. For example, paints, lacquers and varnishes can be tested with respect to color fidelity and maintenance, and also with respect to their mechanical and overall technological behavior. The apparatus has an illumination device with three radiation sectors, which include selectively reflective mirrors, reflecting UV radiation, and being transparent to IR radiation. The selective mirrors extend radially from a common axis outwardly, separating the respective sectors. A IR absorber is located between two each of selectively reflective mirrors of adjacent sectors.

Each one of the three sectors has a xenon radiation source associated therewith to provide the required radiation. This filter-radiation arrangement is surrounded by a quartz inner cylinder with a selectively reflective layer for IR radiation, but passing UV and visible spectral components. A water jacket follows the inner cylinder. The water jacket absorbs long wavelength IR radiation. A quartz outer cylinder, and, eventually, a jacket made of UV special, or window glass, surrounds the structure.

The filter system provides radiation with an energy distribution which very closely matches that of the radiation derived from sunlight. The filtering system largely filters undesired IR components by absorption, and permits passage, selectively, in the short-wave region of a high proportion of radiation to reach the test samples located about the illumination source.

U.S Pat. No. 3,686,940, Kockott, the disclosure of which is incorporated by reference herein and which patent is assigned to an associated organization of the Assignee of the present application, describes a testing apparatus with selective mirrors for removing infrared radiation. The structure has a plurality of eccentrically located radiation sources. A cylindrical mirror is provided which selectively reflects the IR component of the radiation, but is transparent for visible and UV spectral components. Mirrors which are selectively reflective for visible and UV components of the radiation, but passing IR components, are located between the radiation source and the cylindrical mirror. This arrangement permits elimination of short-wave IR radiation, which cause heat, without essentially attenuating the UV radiation.

It has been found that some IR filters, and particularly KG filters, that is, heat absorption filters, when also subjected to UV radiation, change their filtering characteristics. Such filters are particularly desirable and useful to test for resistance to fading, and light effects. These filters have the tendency to change their filtering limit in the UV region towards longer wavelength to such an extent that the desired radiation spectrum is undesirably influenced thereby. The change of the UV limitation is also referred to as aging of the filter.

OBJECT OF THE INVENTION

It is an object to provide a light and weathering resistance test apparatus, particularly to test articles with respect to their resistance to UV and visible spectral light, approaching sunlight, which permits precise adjustment of the respective spectral components and more particularly of IR and UV spectral components and the proportion of visible light within the radiation spectrum. The adjustment should be stable, not subject to change due to aging or the radiation from the source itself. The arrangement should provide a test spectrum for the samples to be tested which matches, as closely as possible, sunlight radiation or a selected spectral distribution, with high efficiency, and with minimum losses due to absorption or reflection.

SUMMARY OF THE INVENTION

Briefly, IR filters, UV filters and UV mirrors are used. Special IR mirrors, which are usual in illumination systems of this type are not needed, however.

A central light source emits radiation in the UV, visible and IR spectral ranges. A sample is positioned, spaced from the central light source in the path of radiation therefrom. The radiation impinging on the sample is controlled by a plurality of UV mirrors, reflecting UV radiation without, essentially, passing UV radiation therethrough, that is, they have a high reflectivity efficiency. At least one UV filter is provided, passing UV radiation and at least one IR filter, passing IR radiation. The region surrounding the light source is subdivided into sectors. In accordance with the invention, a UV filter is located in a first sector and forming a first outer filter; a first mirror-filter combination formed of the first UV mirror having a mirror surface directed towards the light source and an IR filter, essentially congruent with the UV mirror, is provided, the IR filter of the first mirror-filter combination forming a second outer filter. A second mirror-filter combination, and including an essentially congruent sandwich formed by an inner UV mirror having its mirror surface directed towards the light source, an outer UV mirror having its mirror surface directed towards the outer filters, and a IR filter located between the inner and the outer UV mirrors is so located that it places the UV first outer filter entirely within its optical shadow with respect to radiation from the radiation source. The second mirror-filter combination is located spaced from the first mirror-filter combination and positioned between the light source and the first mirror, to direct UV radiation and light to the first UV filter of the first sector. The first UV filter of the first sector thereby forms a radiation window for UV radiation reflected within the spectral control structure from the source, while separating UV radiation from the IR filters, thereby preventing the IR filters from deteriorating under UV light thereon, and preventing aging of the IR filters.

The system has the advantage that a precisely defined radiation spectrum can be obtained with IR filters, UV filters, and UV mirrors, without, however, requiring IR mirrors and without subjecting IR filters to UV radiation so that the IR filters will not age.

The UV filters, referred to in the present specification, are UV limit filters which, in the UV range, have a steep, essentially stable cutoff flank, while being transparent to radiation up to a wavelength of about 2000 nm, that is, they are also transparent for IR radiation. UV mirrors, as used in the present specification, are reflective mirrors which reflect radiation in the UV range of from about 250 to 400 nm; above, and partially below the mirror reflective range, they are transparent to radiation.

DETAILED DESCRIPTION

Figure 1:
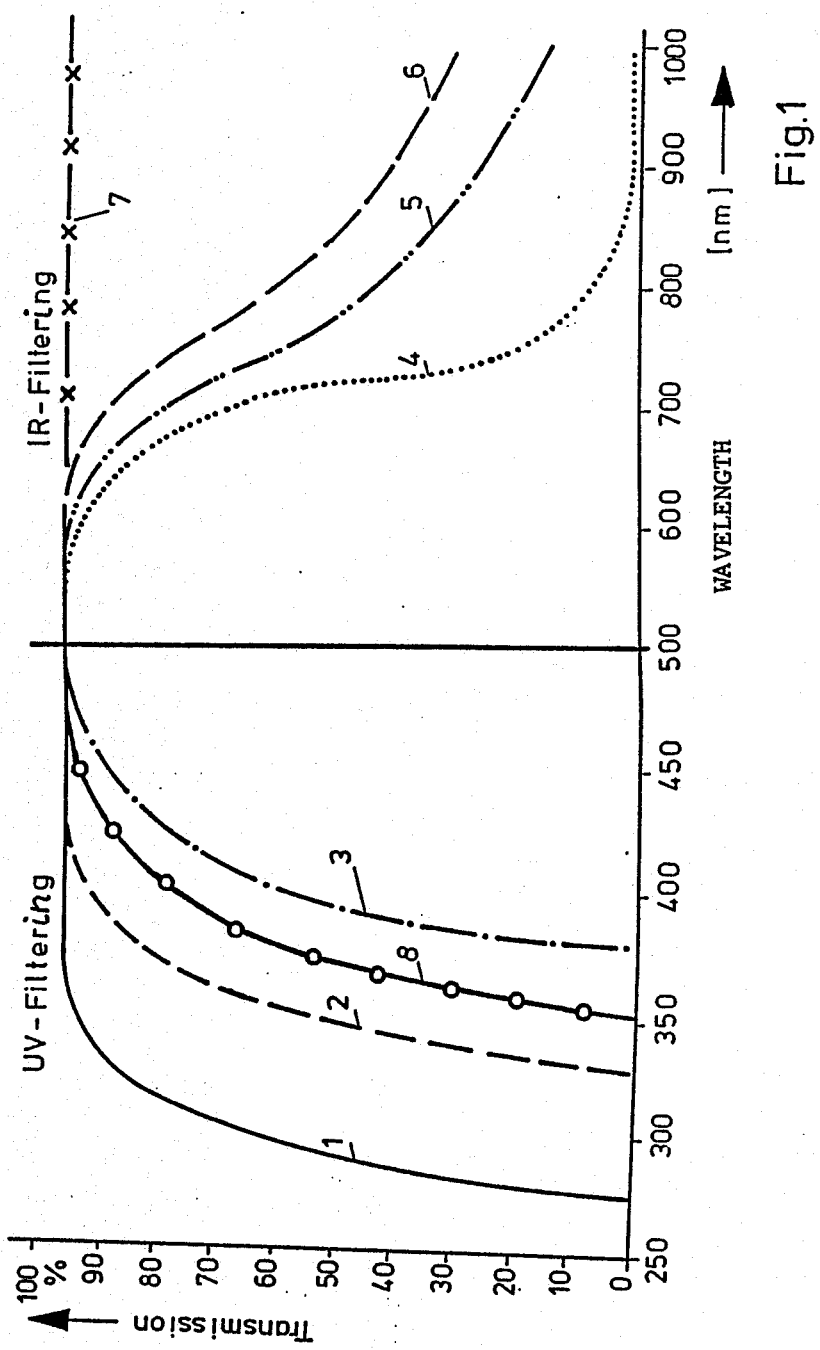
FIG. 1 is a diagram of transmissivity (ordinate) versus wavelength (abscissa) in nm of various UV and IR filters.

FIG. 1 illustrates the filter characteristics of three commercial UV filters 1, 2, 3 and the filter characteristics of three commercial IR filters 4, 5, 6. The transmissivity of the filters is indicated on the ordinate in percent of transmission of radiation, in dependence on wavelength in nm. The typical characteristics 1, 2, 3, for UV filters, show that the flanks are steep and comparatively stable in the UV range. For IR radiation, the curves 1, 2, 3 coincide and the IR radiation can pass essentially unhindered, as shown by the line 7 in FIG. 1. In contrast to the behavior of the UV filters, the IR filters, the characteristics of which are shown at curves 4, 5, 6, do not vary short-wave radiation; rather, the transmissivity of the IR filters ends in a median UV range, as shown by the circle-chain 8 in FIG. 1. Thus, the IR filters also have some UV filtering effect which, however, is not stable.

Figure 2:
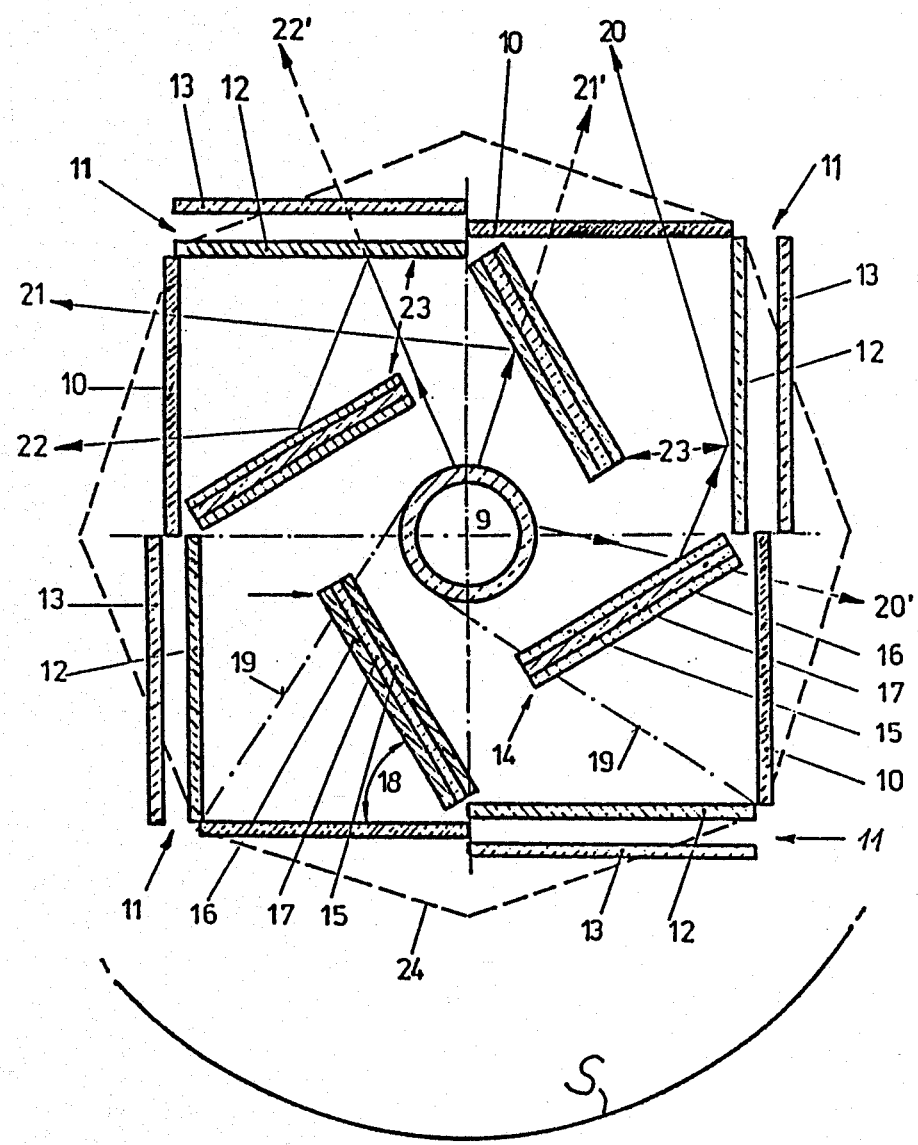
FIG. 2 is a schematic horizontal sectional view through an apparatus in accordance with the present invention, positioned vertically, with outer filters located in a square configuration or, selectively, an octagonal configuration.

The arrangement in accordance with the present invention, in its preferred form, is shown in FIG. 2. The sample S is indicated only schematically, for example a cylindrical support carrier on which paint can be applied, fabric stretched, or the like. The spacing between a central source of radiation 9 and the sample S is not to scale, and would be substantially greater than shown in FIG. 2. The sample S is merely shown for comparison purposes.

The radiation source 9, centrally located in the apparatus, is, preferably, a xenon lamp. It is surrounded by outer filters and mirrors, located in a square configuration. Each side of the square surrounding assembly is subdivided into two sections. The radiation passes through the respective sides—as will appear in greater detail below, through one section having a UV filter 10 and a second section having a first mirror-filter combination 11.

Each one of the first mirror-filter combinations 11 includes a UV mirror 12, having a mirror surface facing the radiation source 9. Congruent with the mirror 12, and at the outside thereof—with respect to the source 9—is a IR filter 13. Filter 13 and mirror 12 form one combination. The UV mirror 12 and the IR filter 13 can be placed adjacent to each other, that is, flat against each other or, as shown in the figure, may be spaced slightly from each other. Suitable holding means and support structures have been omitted from the drawing for clarity, and may be of any suitable construction. In accordance with a feature of the invention, a second mirror-filter combination 14 is provided, located within the outer filters 10 and mirror-filter combinations 11. The second mirror-filter combination 14 is a sandwich construction of three elements, namely an inner UV mirror 15, having a mirror surface directed towards the source 9; an outer UV mirror 16, having a mirror surface directed outwardly; and an intermediate IR filter 17, located between the UV mirrors 15,16. The UV mirrors 15,16 and the IR filter 17 are congruent, for example forming a surface-engaged sandwich. The outer UV filter 10 and the first mirror-filter combination 11 have such a length that they subdivide each side of the rectangular apparatus into two sections of equal length. The second mirror-filter combination 14 extends from the median point of any side of the apparatus, that is, from a line between the transition zone of UV filter 10 to the first mirror-filter combination into the interior space of the apparatus in such a manner that an angle of approximately 50° is formed between the second mirror-filter combination sandwich 14 and the UV filter 10. The angle is shown at 18 with respect to the lower-left mirror-filter combination 14 only, for simplicity of the drawing.

The angle is not critical, and has to be matched to the particular configuration of the section involved, and may vary between about 45° and 80°, as will appear.

The second mirror-filter combination 14 has such a length that the outer UV filter 10, with which it is associated, is entirely within the optical shadow of the second mirror-filter combination 14 with respect to radiation from the source 9. This means that the second mirror-filter combination 14 must extend beyond a connecting line from a corner of the UV filter 10 to a line tangential with the radiation source 9, as shown by chain-dotted line 19 in FIG. 2.

OPERATION AND PATHS OF RADIATION

The entire radiation emitted from the source 9 first impinges on one of the UV filters 12 or 15 of the first or second mirror-filter combination 11,14, respectively. To illustrate the radiation, three selected beams 20,21,22 are shown in the upper portion of the apparatus of FIG. 2. Beam 20 is so selected, that it first impinges on the inner UV mirror 15 of the second mirror-filter combination 14 in the lower right quadrant of the apparatus. The UV portion is reflected, while the IR portion of the emitted radiation is filtered by the IR filter 17 forming the center part of the sandwich 14. The IR portion of the radiation then is transmitted in form of the beam 20' through the UV filter 10.

The UV portion of the beam 20 is reflected by the inner UV mirror 15 of the second mirror-filter combination on the UV mirror 12 of the first mirror-filter combination in the upper-right quadrant of the apparatus, and is emitted through the UV filter 10, as seen at the upper-side of FIG. 2. The UV filter 10 filters the reflected UV beam in desired manner, in accordance with the selected filter. The second mirror-filter combination, by being spaced from the right outer first mirror-filter combination 11, forms a window between the first and second mirror-filter combination. Consequently, beam 20, after dual reflection on the UV mirrors 15 and 12 can pass through the UV filter 10. The window is shown at 23 in FIG. 2.

Beam 21 is reflected only once; a single reflection on the UV mirrors 15 is sufficient to pass beam 21 from the radiation source 9 to the UV filter 10, for filtering therein. The IR portion of beam 21 is filtered by the IR filter 17 in the upper-right quadrant and passes straight out through the UV filter 10 at the upper-right quadrant as beam 21''.

Beam 22, similarly, is separated by the first mirror-filter combination 11 into its UV and IR components, leaving through the IR filter as beam 22', whereas the UV component thereof is reflected by the mirror 12 at the upper-left quadrant, reflected again by the UV mirror 16 at the upper-left quadrant and leaving the apparatus as beam 22 through the UV filter 10 at the upper-left quadrant of the apparatus.

The system can easily be changed by forming the structures not as a rigid square, but, rather, permitting the elements to change, for example to pivot along the horizontal and vertical diammetrical lines—with respect to FIG. 2—to form, selectively, an octagon or a square. The octagonal configuration is shown in broken lines, and either arrangement may be used, as desired, and, for example, the respective sections of the structure can be connected by hinge joints for selective positioning in accordance with a square or an octagon.

The arrangement in accordance with FIGS. 3 to 6 are based on the same principle and, essentially, have the same elements already described, and thus will be provided with the same reference numerals incremented by a "hundred" digit corresponding to the drawing number. The sample S is not shown in the other drawings for simplicity, and can be placed as shown, for example, in FIG. 2, that is concentric to the center of the light source 9.

EMBODIMENT OF FIG. 3

Figure 3:
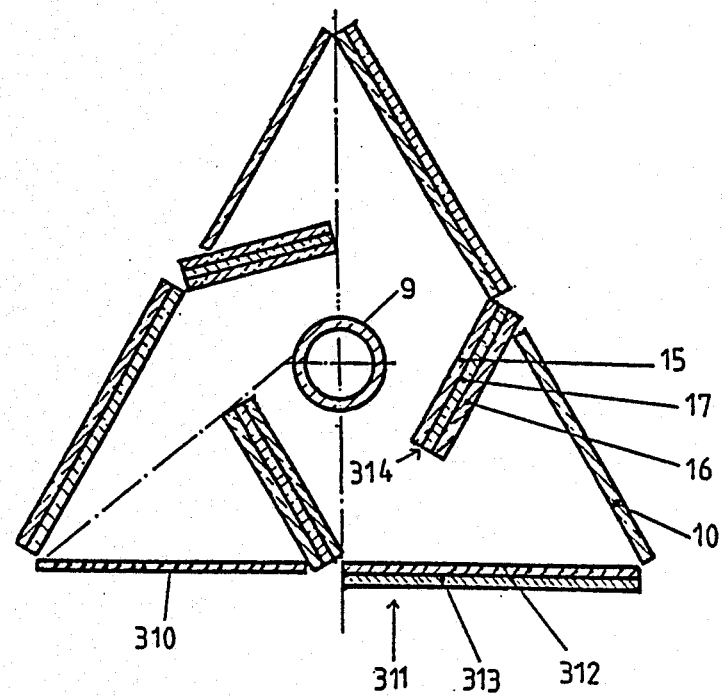
FIG. 3 is a view similar to FIG. 2 with filters arranged in triangular configuration.

An equilateral triangle having three mirror-filter combinations 314 positioned in the interior thereof. The respective separation of the irradiation emitted from the light source to separate UV radiation from the IR component passing through the filters is similar to that described in connection with FIG. 2. FIG. 3 also illustrates the outer UV filter 310, and the first mirror-filter combination 311, in which the mirror element 312, and the filter element 313 are engaged against each other, that is, not spaced as shown in FIG. 2.

EMBODIMENT OF FIG. 4

Figure 4:
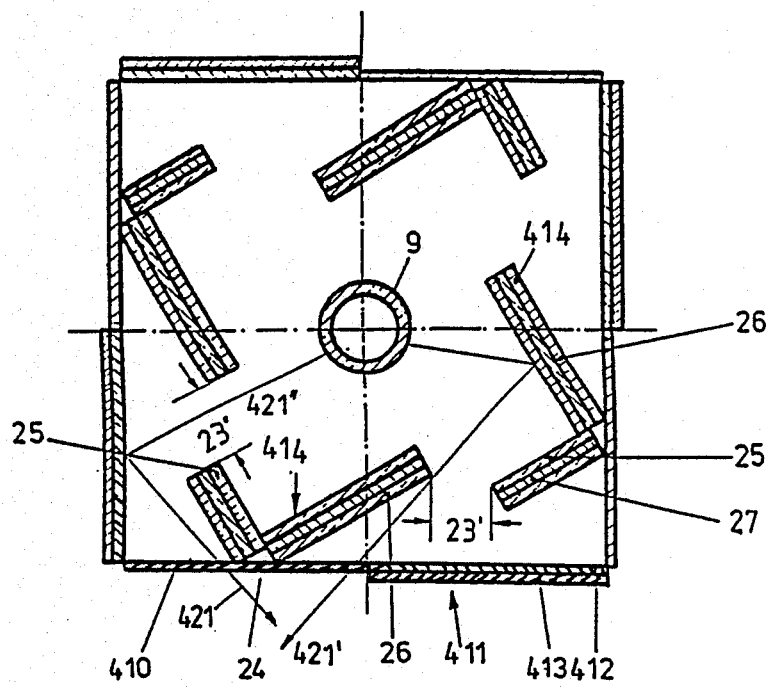
FIG. 4 is a view similar to FIG. 2 with an inner filter arrangement modified with respect to that of FIG. 2.

The general arrangement is similar to that shown in FIG. 2, except that the second mirror-filter combination 414 is divided into two portions 25,26 which, with respect to each other, are located in an essentially V-shaped arrangement, having a tip which touches the outer UV filter 10 at the apex of the V. The IR filter 27 is located between the UV mirrors at the outside of the sandwich. In the arrangement of FIG. 4, windows 23' and 23'' are formed between a portion 25 of one mirror-filter combination 414 and the portion 26 of an adjacent mirror-filter combination 414, as seen at the lower-right quadrant in FIG. 4. The reflected UV radiation can thus pass through the UV filter 10, as shown by beams 421' and 421''. The combination 411 formed of elements 412 and 413 corresponds to the combination of elements 311, 312, 313.

EMBODIMENT OF FIG. 5

The arrangement is constructed, entirely, in cylindrical form. The UV filter 510 and the first-mirror-filter combination 511 are formed as cylinder sectors. Corresponding to FIG. 2, eight sections are provided, formed as eight sectors, which, alternatingly, are formed by a UV filter 510 and a first mirror-filter combination 511. The second mirror-filter combination forming the sandwich 14 can be identical to that shown in FIG. 2. Of course, the IR filter 513, as well as the UV mirror 512, must be curved.

Figure 6:
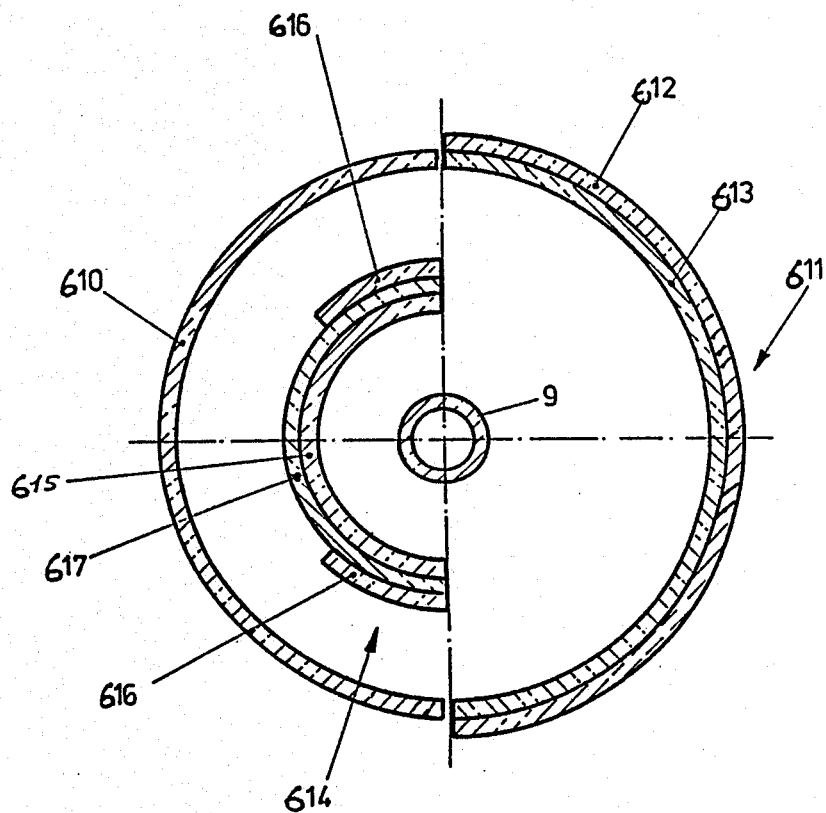
FIG. 6 is a diammetric cross-sectional view of a vertically arranged apparatus with only two sectors.

FIG. 6 illustrates a cylindrical arrangement which has only two sections, forming a half-cylinder 8. A semi-cylindrical—in projection a semi-circular—UV filter 610 is located at the left half of the structure, the right half of the structure being formed by the first mirror-filter combination 611 which, again, in cross-section is semi-circular. The mirror-filter combination is formed by the semi-cylindrical UV filter 612 and the semi-cylindrical IR filter 613. The second mirror-filter sandwich assembly 614 likewise is semi-circular and arranged to place the UV filter 610 entirely in the shadow from the radiation source. In this construction, it is sufficient if the second mirror-filter combination sandwich 614 has the outer UV mirrors 616 applied only along the edge portions thereof; the IR filter 17 and the inner UV mirror 615 extend in the form of a semi-circle or, rather, semi-cylindrical structure around the radiation source 9.

Figure 5:
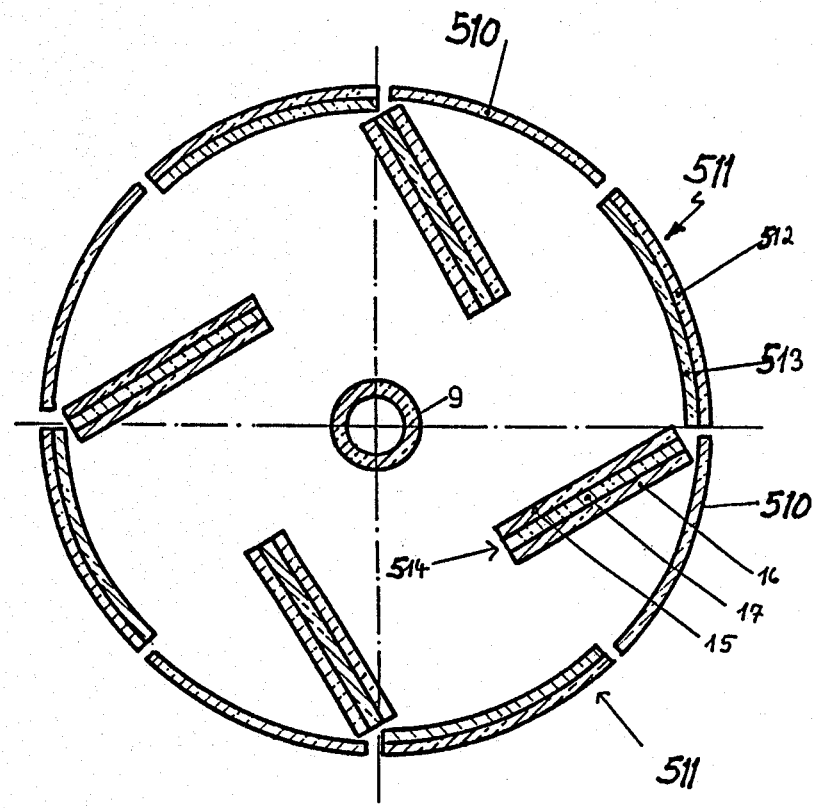
FIG. 5 is a view similar to FIG. 2 with an outer, circular filter system.

The first mirror-filter combination, in which the inner UV mirror 12 has its reflective surface directed towards the radiation source, is congruent with the respective mirror and, preferably, formed as a single, engaged sandwich, as shown by the 311, 411 or 511, FIGS. 3,4,5, for example. UV radiation which impinges on the mirror surface of the UV mirror is reflected back into the interior of the apparatus; visible and IR radiation, however, is permitted to pass through the UV mirror, suitably filtered by the IR filter, and then leaves the apparatus to impinge on the sample S. Thus, UV radiation is separated from the IR filter and cannot cause deterioration thereof.

The second mirror-filter combination has two UV mirrors with externally directed mirror surfaces, between which the IR filter is located. Again, in accordance with a preferred feature of the invention, the mirrors and the filter form one composite sandwich, although the respective elements may be spaced from each other. The UV portion of radiation is reflected away from the IR filter, so that the IR portion and visible radiation from the light source can be passed without essential attenuation, while being filtered with respect to IR radiation in accordance with the IR filter characteristics. Separating the UV portion of the radiation from the IR filter of the second mirror-filter combination 14 protects the filter 17 of the combination. Likewise, the other UV mirrors permit reflection of the UV radiation towards the interior of the system, for emission through the UV filter 10 and impingement on the sample S. If desired, the sample holder for the sample S and the radiation apparatus can be relatively movable, e.g., rotatable.

The basic principle of the arrangement contemplates to separate out the UV component by a UV mirror from the composite radiation received from the radiation source 9 before the radiation impinges on any IR filter or passes through the external or outer UV filter 10. Thus, the UV portion cannot affect the IR filters and cause aging thereof and change of its filtering characteristics. The IR radiation passing through the UV mirror of the first mirror-filter combination 11 is influenced by the IR filter portion 13 thereof. This filter portion may be a KG filter. At least one window, formed between the first and second filter-mirror combination, permits emission only of UV radiation, which had been reflected by a UV mirror at least once. Separating the radiation within the arrangement into the UV component and the IR and visible light component permits filtering only after the respective spectral components have been separated. This permits independent filtering by filters having respective filter flanks or filter characteristics independently of each other. This arrangement, further, permits to obtain any desired precisely defined overall radiation curve, determined by the respective filter characteristics, and hence a precisely defined filtering curve for the overall apparatus while using commercially available filters. Aging effects are essentially avoided, and specifically aging effects of the UV-characteristics of the KG filters, that is, the IR filters, which are highly susceptible to changes in their characteristics when irradiated by UV radiation. The spectral distribution of radiation emitted by the apparatus remains constant, even after long use thereof. The apparatus, additionally, eliminates the use of IR mirrors. IR mirrors are available commercially only in limited spectral reflecting characteristics. The arrangement is highly efficient, since absorption losses are low.

Depending on the irradiation cycles, the illumination apparatus is surrounded by an even number of sections, alternating a UV filter 10 and a first mirror-filter combination 11, so that samples S which are passing around the illumination device are alternately irradiated with UV radiation and, then, with visible and IR radiation, with the IR radiation being controlled in accordance with the respective IR filters being used.

In accordance with a preferred feature of the invention, the second mirror-filter combination 14 is so arranged that the respective UV filter is entirely in the shadow of the second mirror-filter combination 14 with respect to radiation emitted from any point of the light source. As an alternative, the second mirror-filter combination 414 (FIG. 4) can be so arranged that it is divided into two portions 25,26 which are placed at an angle with respect to each other, having an apex 24 located in a median range of the UV filter 410. The lengths of the second mirror-filter combination 414 must have a length sufficiently great that the respective outer UV filter 410 is entirely in the shadow with respect to direct radiation from the source 9.

The arrangement in accordance with FIG. 2 provides for only one window for the passage of UV radiation; in the arrangement of FIG. 4, radiation may pass through two windows as shown in FIG. 9 by beams 421',421".

The specific arrangement and shape of the respective mirror-filter combination is variable. Thus, the outer UV filter 10 and the outer UV mirror-filter combination 11 may be cylindrical, see FIGS. 5,6, or may surround the radiation source in form of a square, an equilateral triangle, an octagon, or the like. Each flat side—if a polygon is used—may be formed of a plurality of first mirror-filter combinations 11, and UV-filters 10. Preferably, however, any one side of any polygon should have only one UV filter 10 and the first mirror-filter combination 11. The preferred arrangement is that of FIG. 2, in which a single second mirror-filter combination 14 is used. The angle between the outer UV filter 10 and the second mirror-filter combination, shown at angle 18, can be between 45° and 80°, preferably between 60° and 70°; smaller angles can be used, however. The arrangement is geometrically particularly desirable, and UV radiation is subjected only to few reflections on the respective UV mirrors before reaching one of the UV filters 10. Consequently, reflection losses, which are unavoidable, are very low, resulting in a high-efficiency apparatus.

Various changes and modifications may be made and features described in connection with any one of the embodiments may be used with any of the others, within the scope of the inventive concept.

I claim:

1. Illumination system for material testing apparatus to test the resistance of a sample (S) to fading, weathering, aging and the like, by irradiation with light of controlled spectral distribution, having a central light source (9) emitting radiation in the ultraviolet (UV), visible, and infrared (IR) spectral ranges, the sample (S) being positioned spaced from the central light source in the path of light therefrom and for irradiation thereby; and means for accurately controlling the radiation spectrum received by the sample, located between the light source (9) and the sample (S), said means including a structure defining a plurality of adjacent sections, the light source being located within said structure, said means comprising, in accordance with the invention a UV filter (10, 310, 410, 510, 610) located in a first section and forming a first outer filter;

a first mirror-filter combination (11,311,411,511,611) located in a second section, and including a first UV mirror (12,312,412,512,612) having its mirror surface directed toward the light source (9) and a first IR filter (13,313,413,513,613), essentially congruent with the first UV mirror, said first IR filter of the first mirror-filter combination forming a second outer filter; and a second mirror-filter combination (14,314,414,514,614) including, in essentially congruent sandwich form, an inner UV mirror (15) having its mirror surface directed towards the light source (9), an outer UV mirror (16) having its mirror surface directed towards the outer filters and an intermediate IR filter (17) located between said inner and outer UV mirrors (15,16), the UV filter (10,310,410,510,610) being positioned entirely within the optical shadow of the second mirror-filter combination (14,314,414,514,614);

and wherein the second mirror-filter combination (14,314,414, 514,614) is located spaced from the first mirror-filter combination (11,311,411,511,611) and positioned in the region of an end zone between the light source (9) and the first mirror-filter combination, and having an end zone positioned to direct UV radiation to the first UV filter (10,310,510,610) of the first section, the first UV filter of the first section thereby forming a radiation window for the UV radiation reflected within the radiation spectrum control means from the source (9) while separating UV radiation from the IR filters, and thereby preventing aging effects of the IR filters when subjected to UV radiation.

2. System according to claim 1, wherein the number of sections is an even number, surrounding the radiation source (9);

and wherein a plurality of UV filters (10,310,410,510) and first mirror-filter combinations (11,311,411,511) are provided, each section, alternatingly, including a UV filter and a first mirror-filter combination.

3. System according to claim 2, wherein the second mirror-filter combination (14,314,414,514) has an end or edge portion located at every second junction between the UV filter (10,310,510) and the first mirror-filter combination (11,311,511), and extends at an angle with respect to the adjacent UV filter dimensioned to place the respective UV filter entirely in the optical shadow of the second mirror-filter combination.

4. System according to claim 3, wherein the sections are located to form, in plan view, a polygon.

5. System according to claim 3, wherein (FIG. 2) the sections are located to form, in plan view, a square, each side of the square including one UV filter (10) and a first mirror-filter combination (11) forming a side of the square, the square surrounding the radiation source.

6. System according to claim 5, wherein the second mirror-filter combination (14) and the outer UV filter (10) include an angle of between 45° and 80°.

7. System according to claim 6, wherein the angle is between 60° and 70°.

8. System according to claim 6, wherein the angle is about 55°.

9. System according to claim 5, wherein each side of the square includes a UV filter (310) and a first mirror-filter combination (311).

10. System according to claim 2, wherein (FIG. 3) the UV filter and the first mirror-filter combination (311), in plan view, form a triangle surrounding the radiation source (9), and wherein one side of the triangle, each, includes alternatingly, a UV filter (10) and a first mirror-filter combination (311).

11. System according to claim 10, wherein each lateral side of the triangle includes a UV filter (310) and a first filter-mirror combination (311).

12. System according to claim 2, wherein (FIG. 4) the second mirror-filter combination (414) comprises two portions (25,26) which are positioned in V-form with respect to each other, the apex (24) of the V-form second mirror-filter combination (414) being located in a median range of the UV filter (10);

and wherein the lengths of the respective portions (25,26) of the second mirror-filter combination (414) are dimensioned to place the respective UV filter (10) entirely within the optical shadow of the second mirror-filter combination (414) with respect to radiation emitted from said radiation source (9).

13. System according to claim 1, wherein (FIGS. 5,6) the UV filter (510,610) and the first mirror-filter combination (514,614) are cylindrical and cylindrically surround the radiation source (9).

14. System according to claim 13, wherein (FIG. 5) a plurality of alternatingly, adjacently located UV filters (510) and first mirror-filter combinations (514) are provided, each forming a part-cylindrical surface of said radiation spectrum control means.

15. System according to claim 14, wherein the second mirror-filter combination (514) has an end or edge portion located at every second junction between the UV filter (510) and the first mirror-filter combination (511), and extends at an angle with respect to the adjacent UV filter dimensioned to place the respective UV filter entirely in the optical shadow of the second mirror-filter combination.

16. System according to claim 13, wherein (FIG. 6) the UV filter, in plan view, is a semi-circular filter and, defining a semi-cylindrical filter element, and the first mirror-filter combination, in plan view, is semi-circular and defines a semi-cylindrical element (614), said two semi-cylindric elements being joined to form one essentially cylindrical surface, cylindrically surrounding the radiation source (9).

17. System according to claim 16, wherein the second mirror-filter combination (614) is essentially, in plan view, semi-cylindrical;

and wherein the outer UV mirror (616) of the second mirror-filter combination (614) comprises two separated mirror elements located adjacent the circular end regions of the half-cylinder formed by the second mirror-cylinder combination.

* * * * *